(12) United States Patent
Dong et al.

(10) Patent No.: US 9,302,005 B2
(45) Date of Patent: Apr. 5, 2016

(54) METHODS AND MATERIALS FOR TREATING CANCER

(71) Applicant: Mayo Foundation for Medical Education and Research, Rochester, MN (US)

(72) Inventors: Haidong Dong, Rochester, MN (US); Eugene D. Kwon, Rochester, MN (US); Svetomir N. Markovic, Rochester, MN (US); Christopher J. Krco, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 114 days.

(21) Appl. No.: 14/192,376

(22) Filed: Feb. 27, 2014

(65) Prior Publication Data
US 2014/0271674 A1   Sep. 18, 2014

Related U.S. Application Data

(60) Provisional application No. 61/786,199, filed on Mar. 14, 2013.

(51) Int. Cl.
| A61K 45/00 | (2006.01) |
| C07K 14/705 | (2006.01) |
| A61K 35/17 | (2015.01) |

(52) U.S. Cl.
CPC ........... *A61K 45/00* (2013.01); *C07K 14/70532* (2013.01); *A61K 35/17* (2013.01)

(58) Field of Classification Search
None
See application file for complete search history.

(56) References Cited

PUBLICATIONS

Kim et al., 2010, Curr Opin Immunol.; 22(2): 223-230.*
Duraiswamy et al., Oct. 1, 2013;2(10):e25912, 3 pages.*
McDermott et al., 2013, Cancer Medicine; 2(5): 662-673.*
Ahmadzadeh et al., "Tumor antigen-specific CD8 T cells infiltrating the tumor express high levels of PD-1 and are functionally impaired," *Blood*, 114(8):1537-1544, Epub May 7, 2009.
Anikeeva et al., "Distinct role of lymphocyte function-associated antigen-1 in mediating effective cytolytic activity by cytotoxic T lymphocytes," *Proc Natl Acad Sci U S A.*, 102(18):6437-6442, Epub Apr. 25, 2005.
Barber et al., "Restoring function in exhausted CD8 T cells during chronic viral infection," *Nature*, 439(7077):682-687, Epub Dec. 28, 2005.
Betts et al., "Sensitive and viable identification of antigen-specific CD8+ T cells by a flow cytometric assay for degranulation," *J Immunol Methods.*, 281(1-2):65-78, Oct. 1, 2003.
Blank et al., "PD-L1/B7H-1 inhibits the effector phase of tumor rejection by T cell receptor (TCR) transgenic CD8+ T cells," *Cancer Res.*, 64(3):1140-1145, Feb. 1, 2004.
Boggio et al., "Interleukin 12-mediated prevention of spontaneous mammary adenocarcinomas in two lines of Her-2/neu transgenic mice," *J Exp Med.*, 188(3):589-596, Aug. 3, 1998.
Brinkmann et al., "FTY720: altered lymphocyte traffic results in allograft protection," *Transplantation.*, 72(5):764-769, Sep. 15, 2001.
Crispe, "Hepatic T cells and liver tolerance," *Nat Rev Immunol.*, 3(1):51-62, Jan. 2003.
Dong and Chen, "B7-H1 pathway and its role in the evasion of tumor immunity," *J Mol Med (Berl).*, 81(5):281-287, Epub Apr. 30, 2003.
Dong et al., "B7-H1 determines accumulation and deletion of intrahepatic CD8(+) T lymphocytes," *Immunity.*, 20(3):327-336, Mar. 2004.
Dong et al., "Tumor-associated B7-H1 promotes T-cell apoptosis: a potential mechanism of immune evasion," *Nat Med.*, 8(8):793-800, Epub Jun. 24, 2002.
GenBank® Accession No. AAH74740.1, GI No. 49902307, "Programmed cell death 1 [*Homo sapiens*]," Jul. 15, 2006, 2 pages.
GenBank® Accession No. AAX29153.1, GI No. 60652917, "integrin alpha L, partial [synthetic construct]," Mar. 29, 2005, 2 pages.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 Image:3142951), complete cds," 4 pages, (2005).
GenBank® Accession No. BC074740.2, GI No. 50960296, "*Homo sapiens* programmed cell death 1, mRNA (cDNA clone MGC:103817 Image:30915198), complete cds," Jul. 15, 2006, 3 pages.
Gibbons et al., "B7-H1 limits the entry of effector CD8(+) T cells to the memory pool by upregulating Bim," Oncoimmunology, 1(7):1061-1073, Oct. 1, 2012.
Harrington et al., "Differentiating between memory and effector CD8 T cells by altered expression of cell surface O-glycans," *J Exp Med.*, 191(7):1241-1246, Apr. 3, 2000.
Iwai et al., "Involvement of PD-L1 on tumor cells in the escape from host immune system and tumor immunotherapy by PD-L1 blockade," *Proc Natl Acad Sci U S A.*, 99(19):12293-12297, Epub Sep. 6, 2002.
Katou et al., "Differing phenotypes between intraepithelial and stromal lymphocytes in early-stage tongue cancer," *Cancer Res.*, 67(23):11195-11201, Dec. 1, 2007.

(Continued)

*Primary Examiner* — Ilia Ouspenski
(74) *Attorney, Agent, or Firm* — Fish & Richardson P.C.

(57) ABSTRACT

This document provides methods and materials involved in treating cancer. For example, methods and materials for identifying a mammal as having an elevated level of PD-1$^+$/CD11a$^{high}$ CD8 T cells having the potential to exert anti-cancer effects are provided. In addition, methods and materials for identifying a mammal as having an elevated level of PD-1$^+$/CD11a$^{high}$ CD8 T cells and administering a PD-1 inhibitor to such a mammal are provided.

7 Claims, 9 Drawing Sheets

(56) References Cited

PUBLICATIONS

Lazarevic and Glimcher, "T-bet in disease," *Nat Immunol.*, 12(7):597-606, Jun. 20, 2011.

Lewis et al., "Surrogate tumor antigen vaccination induces tumor-specific immunity and the rejection of spontaneous metastases," *Cancer Res.*, 65(7):2938-2946, Apr. 1, 2005.

Lunsford et al., "Targeting LFA-1 and cd154 suppresses the in vivo activation and development of cytolytic (cd4-Independent) CD8+ T cells," *J Immunol.*, 175(12):7855-7866, Dec. 15, 2005.

Mumprecht et al., "Programmed death 1 signaling on chronic myeloid leukemia-specific T cells results in T-cell exhaustion and disease progression," *Blood.*, 114(8):1528-1536. Epub May 6, 2009.

Nava-Parada et al., "Peptide vaccine given with a Toll-like receptor agonist is effective for the treatment and prevention of spontaneous breast tumors," *Cancer Res.*, 67(3):1326-1334, Feb. 1, 2007.

Rai et al., "Tracking the total CD8 T cell response to infection reveals substantial discordance in magnitude and kinetics between inbred and outbred hosts," *J Immunol.*, 183(12):7672-7681, Dec. 15, 2009.

Schmidt et al., "Extreme CD8 T cell requirements for anti-malarial liver-stage immunity following immunization with radiation attenuated sporozoites," *PLoS Pathog.*, 6(7):e1000998, Jul. 15, 2010.

Schmits et al., "LFA-1-deficient mice show normal CTL responses to virus but fail to reject immunogenic tumor," *J Exp Med.*, 183(4):1415-1426, Apr. 1, 1996.

Seki et al., "Tumor-specific CTL kill murine renal cancer cells using both perforin and Fas ligand-mediated lysis in vitro, but cause tumor regression in vivo in the absence of perforin," *J Immunol.*, 168(7):3484-3492, Apr. 1, 2002.

Smith et al., Differential outcome of IL-2/anti-IL-2 complex therapy on effector and memory CD8+ T cells following vaccination with an adenoviral vector encoding EBV epitopes, *J Immunol.*, 186(10):5784-5790, Epub Apr. 11, 2011.

Thompson et al., "PD-1 is expressed by tumor-infiltrating immune cells and is associated with poor outcome for patients with renal cell carcinoma," *Clin Cancer Res.*, 13(6):1757-1761, Mar. 15, 2007.

Thompson et al., "Tumor masses support naive T cell infiltration, activation, and differentiation into effectors," *J Exp Med.*, 207(8):1791-1804, Epub Jul. 26, 2010.

Truneh et al., "Early steps of lymphocyte activation bypassed by synergy between calcium ionophores and phorbol ester," *Nature.*, 313(6000):318-320, Jan. 24-30, 1985.

Vesely et al., "Natural innate and adaptive immunity to cancer," *Annu Rev Immunol.*, 29:235-271, 2011.

Zhang et al., "PD-1/PD-L1 interactions inhibit antitumor immune responses in a murine acute myeloid leukemia model," *Blood*, 114(8):1545-1552, Epub May 5, 2009.

\* cited by examiner

METHODS AND MATERIALS FOR TREATING CANCER

CROSS-REFERENCE TO RELATED APPLICATIONS

This application claims the benefit of U.S. provisional application 61/786,199, filed Mar. 14, 2013. The disclosure of the prior application IS considered part of (and is incorporated by reference in) the disclosure of this application.

BACKGROUND

1. Technical Field

This document relates to methods and materials involved in treating cancer. For example, this document provides methods and materials for identifying a mammal as having an elevated level of CD8 T cells that express PD-1 and CD11a polypeptides (PD-1$^+$/CD11a$^{high}$ CD8 T cells) and administering a PD-1 inhibitor to such a mammal.

2. Background Information

CD11a (LFA-1, lymphocyte functional-associated antigen 1) is a polypeptide expressed by T cells. It binds to ICAM-1 on antigen-presenting cells and functions as an adhesion molecule. CD11a is indispensable in mediating conjugation of cytotoxic T lymphocytes (CTLs) and target cells. Blocking CD11a can dramatically reduce the killing of tumor cells and rejecting of transplants by CTLs.

B7-H1 is a polypeptide expressed by a variety of tumor cells. It also is constitutively expressed by macrophages and dendritic cells, its expression being up-regulated upon cell activation. PD-1 is a receptor for B7-H1 polypeptides.

SUMMARY

This document provides methods and materials involved in treating cancer. For example, this document provides methods and materials for identifying a mammal as having an elevated level of PD-1$^+$/CD11a$^{high}$ CD8 T cells having the potential to exert anti-cancer effects. In some cases, this document provides methods and materials for identifying a mammal as having an elevated level of PD-1$^+$/CD11a$^{high}$ CD8 T cells and administering a PD-1 inhibitor to such a mammal. Administration of a PD-1 inhibitor to a mammal having an elevated level of PD-1$^+$/CD11a$^{high}$ CD8 T cells can result in naturally-occurring tumor-reactive CD8 CTLs present within the PD-1$^+$/CD11a$^{high}$ CD8 T cell population exerting anti-cancer effects against cancer cells present within the mammal.

Having the ability to identify mammals with cancer that have an elevated level of PD-1$^+$/CD11a$^{high}$ CD8 T cells can allow clinicians to identify those cancer patients having the potential to exert anti-cancer effects against cancer cells present within the mammal. Once identified, a cancer patient having an elevated level of PD-1$^+$/CD11a$^{high}$ CD8 T cells can be administered a PD-1 inhibitor under conditions wherein naturally-occurring tumor-reactive CD8 CTLs present within the PD-1$^+$/CD11a$^{high}$ CD8 T cell population exert anti-cancer effects against cancer cells present within the mammal.

In general, one aspect of this document features a method for treating a mammal having cancer. The method comprises, or consists essentially of, (a) identifying the mammal as having an elevated level of PD-1$^+$/CD11a$^{high}$ CD8 T cells within a sample (e.g., a blood, body fluid, or tumor sample), and (b) administering a PD-1 inhibitor to the mammal under conditions wherein naturally-occurring tumor-reactive CD8 CTLs within a PD-1$^+$/CD11a$^{high}$ CD8 T cell population of the mammal are triggered to exert an anti-cancer effect against the cancer. The mammal can be a human. The elevated level can be determined using flow cytometry. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

In another aspect, this document features a method for treating cancer. The method comprises, or consists essentially of, administering a PD-1 inhibitor to a mammal identified as having an elevated level of PD-1$^+$/CD11a$^{high}$ CD8 T cells within a sample (e.g., a blood, body fluid, or tumor sample), wherein the PD-1 inhibitor is administered under conditions wherein naturally-occurring tumor-reactive CD8 CTLs within a PD-1$^+$/CD11a$^{high}$ CD8 T cell population of the mammal are triggered to exert an anti-cancer effect against the cancer. The mammal can be a human. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
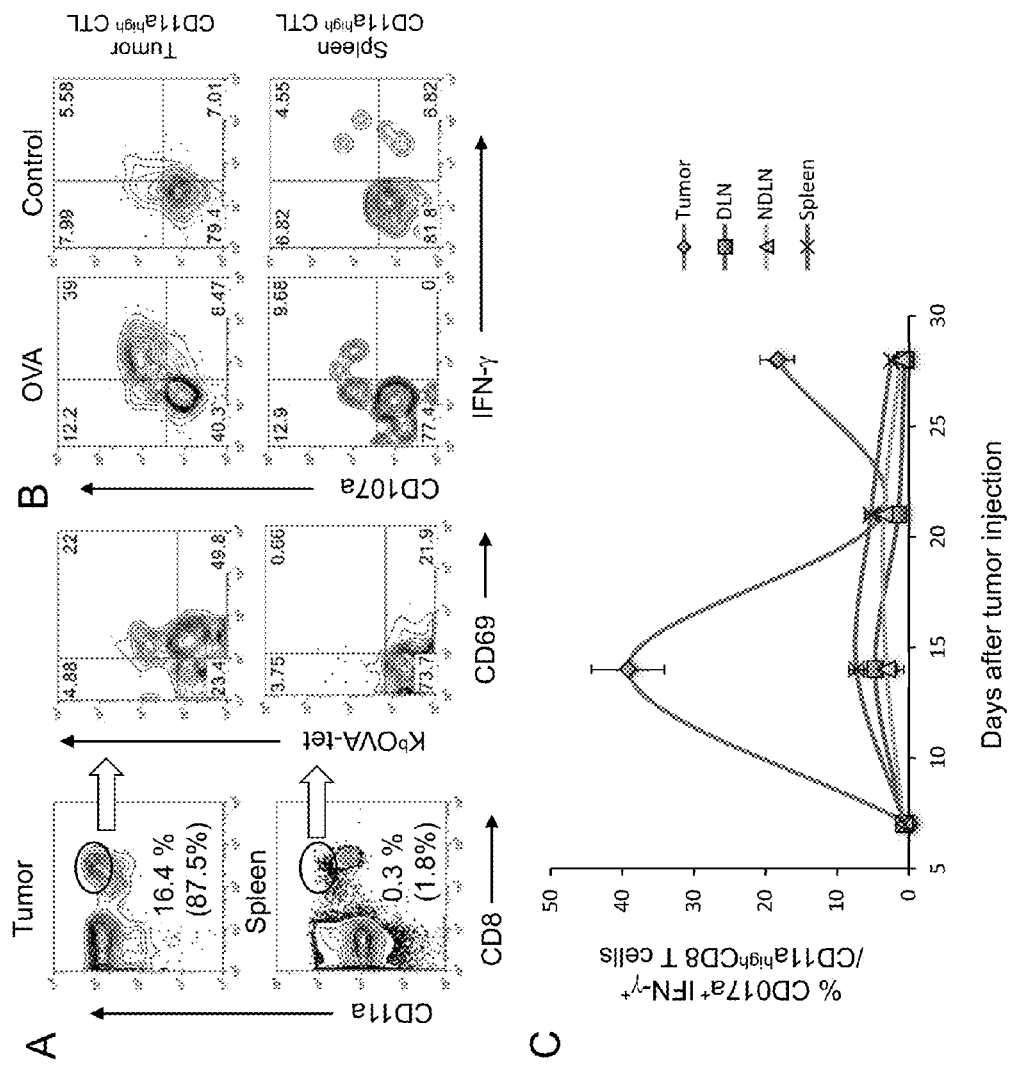
FIG. 1. Naturally-occurring tumor-specific CD8 T cells in tumor tissues. B16-OVA tumor cells were subcutaneously injected into naïve C57BL/6 mice. (A) On day 14 after tumor injection, lymphocytes were isolated from tumor tissues and spleen and were stained with antibodies for CD8, CD11a, CD69 and K$^b$OVA-tetramer. For measuring CTL activity, cells were incubated with OVA or control peptides for five hours in the presence of anti-CD107a antibody and followed by intracellular staining for IFN-γ. Data show the percentages of CD11a$^{high}$ CD8 T cells in whole tumor tissues and spleen. Percentages in parentheses indicate the percent of CD11a$^{high}$ subset per CD8 T cells. One of three independent experiments is shown. (B) The kinetics and distributions of functional CD11a$^{high}$ CD8 T cells in tumor tissues, draining lymph nodes (DLN) and non-draining lymph nodes (NDLN) and spleen. Data show the average percent ±SD of CD107a$^+$ IFN-γ$^+$ per CD11a$^{high}$ CD8 T cells (n=3). (C) A graph plotting the percentage of the indicated cells vs. time post tumor injection.

This document provides methods and materials involved in treating cancer. For example, this document provides methods and materials for identifying a mammal as having an elevated level of PD-1$^+$/CD11a$^{high}$ CD8 T cells. As described herein, cancer patients having an elevated level of PD-1$^+$/CD11a$^{high}$ CD8 T cells can have an increased potential to exert anti-cancer effects. For example, cancer patients having an elevated level of PD-1$^+$/CD11a$^{high}$ CD8 T cells can have a population of naturally-occurring tumor-reactive CD8 CTLs with the capability of being triggered to exert anti-cancer effects against cancer cells present within the cancer patient.

The term "elevated level" as used herein with respect to a level of PD-1$^+$/CD11a$^{high}$ CD8 T cells refers to any level that is greater than a reference level of PD-1$^+$/CD11a$^{high}$ CD8 T cells. The term "reference level" as used herein with respect to PD-1$^+$/CD11a$^{high}$ CD8 T cells refers to the level of PD-1$^+$/CD11a$^{high}$ CD8 T cells typically observed in peripheral blood of healthy mammals without cancer. For example, a reference level of PD-1$^+$/CD11a$^{high}$ CD8 T cells can be the average number of PD-1$^+$/CD11a$^{high}$ CD8 T cells present in the peripheral blood obtained from a random sampling of 50 humans free of cancer. In some cases, an elevated level of PD-1$^+$/CD11a$^{high}$ CD8 T cells can be a level that is at least 10, 25, or 50 percent greater than a reference level of PD-1$^+$/CD11a$^{high}$ CD8 T cells.

In some cases, the presence of an elevated level of PD-1$^+$/CD11a$^{high}$ CD8 T cells can be determined using cell frequencies. For example, the presence of more than 20 PD-1$^+$/CD11a$^{high}$ CD8 T cells per 100 CD8 T cells within a peripheral blood sample can be an elevated level of PD-1$^+$/CD11a$^{high}$ CD8 T cells. It will be appreciated that levels from comparable samples are used when determining whether or not a particular level is an elevated level.

As described herein, the level of PD-1$^+$/CD11a$^{high}$ CD8 T cells present within a blood sample (e.g., a peripheral blood sample) can be used to determine whether or not a particular mammal has an increased potential to exert anti-cancer effects via CTLs. Any appropriate T cell-containing sample can be used as described herein to identify mammals having an elevated level of PD-1$^+$/CD11a$^{high}$ CD8 T cells. For example, tumor tissue samples, ascites samples, and lymphoid organ sample can be used to determine whether or not a mammal has an elevated level of PD-1$^+$/CD11a$^{high}$ CD8 T cells.

Any appropriate methods can be used to determine the level of PD-1$^+$/CD11a$^{high}$ CD8 T cells within a sample. For example, antibody staining techniques such an immunohistochemistry or flow cytometry can be used to determine whether or not a particular sample contains an elevated level of PD-1$^+$/CD11a$^{high}$ CD8 T cells.

Examples of anti-human PD-1 antibodies that can be used to identify PD-1$^+$/CD11a$^{high}$ CD8 T cells include, without limitation, anti-human PD-1 antibodies commercially available from Biolegend (Catalog Nos. 329904 or 329905; San Diego, Calif.) or eBioscience (Catalog No. 12-2799-42; San Diego, Calif.).

Examples of anti-human CD11a antibodies that can be used to identify PD-1$^+$/CD11a$^{high}$ CD8 T cells include, without limitation, anti-human CD11a antibodies commercially available from Biolegend (Catalog Nos. 301212 or 350604; San Diego, Calif.) or Novus (Catalog No. NB500-309; Littleton, Colo.).

Examples of anti-human CD8 antibodies that can be used to identify PD-1$^+$/CD11a$^{high}$ CD8 T cells include, without limitation, anti-human CD8 antibodies commercially available from BD Bioscience (Catalog No. 557851; San Jose, Calif.).

Examples of a human PD-1 nucleic acid can have the sequence set forth in GenBank® Accession No. BC074740.2 (GI No. 50960296), and a human PD-1 polypeptide can have the sequence set forth in GenBank® Accession No. AAH74740.1 (GI No. 49902307). Examples of a human CD11a nucleic acid can have the sequence set forth in GenBank® Accession No. BC008777.2 (GI No. 33870544), and a human CD11a polypeptide can have the sequence set forth in GenBank® Accession No. AAX29153.1 (GI No. 60652917).

Once the level (or frequency) of PD-1$^+$/CD11a$^{high}$ CD8 T cells within a sample from a mammal is determined, the level can be compared to a cut-off level, a cut-off frequency, or a reference level and used to classify the mammal as having or lacking an elevated level of PD-1$^+$/CD11a$^{high}$ CD8 T cells.

Once identified as having an elevated level of PD-1$^+$/CD11a$^{high}$ CD8 T cells as described herein, the mammal can be administered a PD-1 inhibitor. Examples of PD-1 inhibitors included, without limitation, anti-PD-1 antibodies, anti-PD-1 ligand antibodies, PD-1 fusion proteins, PD-1 siRNA, and PD-1 miRNA.

Administration of a PD-1 inhibitor to a mammal having an elevated level of PD-1$^+$/CD11a$^{high}$ CD8 T cells can result in naturally-occurring tumor-reactive CD8 CTLs present within the PD-1$^+$/CD11a$^{high}$ CD8 T cell population exerting anti-cancer effects against cancer cells present within the mammal.

In some cases, the presence of PD-1$^+$/CD11a$^{high}$ CD8 T cells in a cancer patient can represent a pre-existing immunity to cancer. In such cases, this population of T cells can represent a means to identify patients whose immune systems have already been primed by tumor antigens, yet are not able to exert an effective antitumor immunity. Such patients can be identified as described herein and can be treated with a PD-1 inhibitor to reduce the number of cancer cells present in that patient.

The invention will be further described in the following examples, which do not limit the scope of the invention described in the claims.

EXAMPLES

Example 1

B7-H1 Limits the Entry of Effector CD8$^+$ T Cells to the Memory Pool by Upregulating Bim In immunized B7-H1-deficient mice, an increased expansion of effector CD8$^+$ T cells and a delayed T cell contraction followed by the emergence of a protective CD8$^+$ T cell memory capable of completely rejecting tumor metastases in the lung were detected. Intracellular staining revealed that antigen-primed CD8$^+$ T cells in B7-H1-deficient mice express lower levels of the pro-apoptotic molecule Bim. The engagement of activated CD8$^+$ T cells by a plate-bound B7-H1 fusion protein led to the upregulation of Bim and increased cell death. Assays based on blocking antibodies determined that both PD-1 and CD80 are involved in the B7-H1-mediated regulation of Bim in activated CD8$^+$ T cells. See, also, Gibbons et al., *Oncoimmunology*, 1(7):1061-1073 (2012). These results suggested that B7-H1 negatively regulates CD8$^+$ T cell memory by enhancing the depletion of effector CD8$^+$ T cells through the upregulation of Bim.

Example 2

Natural Occurring Tumor-reactive CD8 T Cells are Differentiated Effector Cells with High Expression of CD11a and PD-1

Mice, Cell Lines and Reagents

Female C57BL/6 and Balb/c mice were purchased from Taconic Farms (Germantown, N.Y.). PD-1 knockout (KO) C57BL/6 mice were obtained from L. Chen (Yale University, New Haven, Conn.) with the permission of Dr. T. Honjo (Kyoto University). Mice were maintained under pathogen-free conditions and used at 8-12 weeks of age. Tumor tissues and spleen samples from Balb-neuT mice were obtained from Dr. L. Pease (Mayo Clinic, Rochester). B16-OVA murine melanoma cells were obtained from R. Vile (Mayo Clinic, Rochester, Minn.), 4T1 tumor cells were purchased from ATCC and were cultured in RPMI 1640 medium (Cellgro, Hendon, Va.) with 10% FBS (Life Technologies, Carlsbad, Calif.), 1 U/mL penicillin, 1 μg/mL streptomycin, and 20 mM HEPES buffer (all from Mediatech, Manassas, Va.). FTY720 was obtained from Cayman Chemical (Ann Arbor, Mich.). PMA and Ionomycin were obtained from Sigma.

Flow Cytometry Analysis

Class I MHC (K$^b$OVA peptide: SIINFEKL (SEQ ID NO:1)) tetramer and control tetramer (mock-loaded) were obtained from Beckman Coulter (Brea, Calif.). Fluorochrome-conjugated Abs against CD3, CD8, CD11a (M17/4), CD69, PD-1, CD62L, T-bet, Foxp-3, Ki67, CD107a, and IFN-γ were obtained from BD Biosciences (Mountain View, Calif.), BioLegend (San Diego, Calif.), or eBioscience (San Diego, Calif.). To detect intracellular IFN-γ levels, cells were incubated with GolgiPlug (BD Biosciences) for four hours prior to analysis. Cells were stained for surface antigens and then incubated in Fixation Buffer (BioLegend) for 20 minutes at room temperature, followed by permeabilization using Permeabilization Wash Buffer (BioLegend). To detect the intranuclear levels of Ki67, T-bet, and Foxp 3, T cells were first stained for surface antigens (CD8 and CD11a), fixed, and then permeabilized by Foxp3 buffer kit according to the manufacture's protocol (eBioScience). After staining, cells were washed three times with washing buffer before analysis. At least 100,000 viable cells were live gated on FACScan or FACSCailbur (BD Biosciences, USA) instrumentation. Flow cytometry analysis was performed using FlowJo software (Tree Star, Ashland, Oreg.).

Cytotoxic T Lymphocyte (CTL) Function Assay

Degranulation of CTLs was measured by CD 107a mobilization (Betts et al., *J. Immunol. Methods.*, 281:65-78 (2003)) followed by intracellular staining for IFN-γ. Briefly, lymphocytes were incubated with OVA peptide$_{257-264}$ (Mayo Clinic Peptide Core) at 1 μg/mL, or PMA (50 ng/mL)/Ionomycin (500 ng/mL) for four hours in the presence of anti-CD107a. After incubation, cells were stained for CD8 and CD11a followed by intracellular staining for IFN-γ.

Tumor Studies

Mice were inoculated subcutaneously or intravenously with 5×10⁵ wild type or PD-1 KO B16-OVA tumor cells in C57BL/6 mice or 1×10⁵ 4T1 tumor cells in BalB/c mice. A caliper was used to measure the length and width of tumors twice a week. Some mice were intraperitoneally injected with FTY720 (1 mg/kg) every two days over a week. On indicated days after tumor injection, tumor tissues and lymphoid organs were removed and incubated in digestion buffer (RPMI medium containing 5% fetal bovine serum, 0.02% Collagenase IV, 0.002% DNase I and 10 U/mL of Heparin) for 40 minutes followed with isolation of lymphocytes.

Detection of Melanoma Specific Human CD8 T Cells

Peripheral blood mononuclear cells (PBMC) samples were collected from HLA-A2 positive patients with stage IV melanoma. Cells were stained with antibodies for CD8, CD11a, PD-1 (MIH4), and CTLA-4 (BD Bioscience and eBioscience, CA, USA). To detect melanoma antigen-specific CD8 T cells, PBMCs were stained with HLA-A2/MART-1 Tetramer (Beckman Coulter, Brea, Calif.).

Statistical Analysis

All statistical analyses were performed using GraphPad Prism software 5.0 (GraphPad Software, Inc., San Diego, Calif.). A two-sided, unpaired or paired Student T test was used to assess statistical differences in experimental groups. A p value <0.05 was considered statistically significant.

Results

CD11a$^{high}$ CD8 T Cells Form an Antitumoral T Cell Population

The presence of CD11a$^{high}$ CD8 T cells in mice harboring a subcutaneously growing tumor was monitored, and corresponding antigen-specific CTL function was analyzed. B16-OVA tumor cells which express a surrogate tumor antigen OVA (ovalbumin) were subcutaneously injected into naïve B6 mice. On day 7 after tumor injection, lymphocytes were isolated from tumor tissues, draining lymph nodes (DLN), non-draining lymph nodes (NDLN), and spleen. The expression of CD11a on CD8 T cells was examined by flow cytometry in freshly isolated lymphocytes from tumor or lymphoid tissues. CD11a$^{high}$ CD8 T cells were primarily detected within tumor tissue and were largely absent in the spleen, suggesting the accumulation of CD11a$^{high}$ CD8 T cells is tumor-associated (FIG. 1A). The antigen-specificity and activation status of CD11a$^{high}$ CD8 T cells were ascertained by staining using K$^b$OVA-tetramer and anti-CD69 antibody (FIG. 1A). Most tumor infiltrating CD11a$^{high}$ CD8 T cells within tumors were CD69 positive, and 54% of them were K$^b$OVA tetramer positive (FIG. 1A), while fewer spleen CD11a$^{high}$ CD8 T cells were K$^b$OVA tetramer positive even though a portion of them were CD69 positive. Cytotoxic T lymphocyte (CTL) capacity of CD11a$^{high}$ CD8 T cells was analyzed by measuring degranulation (CD107a expression) and IFN-γ production following a brief stimulation with OVA or control peptides ex vivo. CD11a$^{high}$ CD8 T cells from tumor site demonstrated degranulation and IFN-γ production following stimulation with OVA antigen peptide, but not with control peptide (FIG. 1B). In contrast, spleen CD11a$^{high}$ CD8 T cells exhibited weaker CTL function compared with tumor CD11a$^{high}$ CD8 T cells. These results suggested that CD11a$^{high}$ CD8 T cells are mainly identified within tumors and that they are effector CTLs responding to specific tumor antigens.

Tracking the kinetics and distribution of CD11a$^{high}$ CD8 T cells in tumor-bearing host, functional (CD107a⁺IFN-γ⁺) CD11a$^{high}$ CD8 T cells were determined to peak within tumors on day 14 after tumor injection and progressively diminished in frequency over the next seven day (FIG. 1C). Interestingly, functional CD11a$^{high}$ CD8 T cells increased in numbers thereafter as the tumor grew, and the mice euthanized at day 28 (FIG. 1C). In contrast, functional CD11a$^{high}$ CD8 T cells were barely found in tumor-draining lymph nodes (DLN), non-DLN, and spleen from day 7 through day 28 after tumor injection. These results led to the conclusion that CD11a$^{high}$ CD8 T cells represent tumor-specific and tumor-reactive functional CD8 CTLs in tumor sites.

Figure 2:
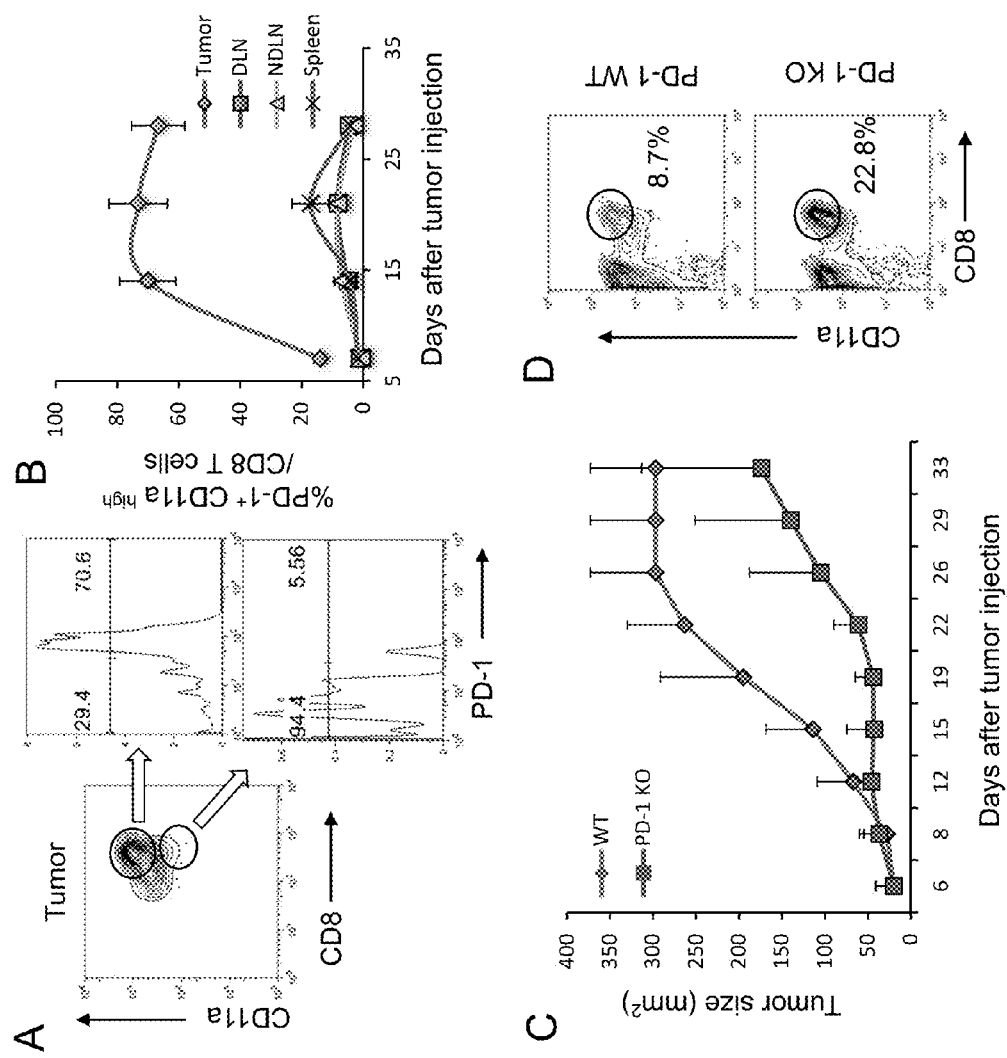
FIG. 2. PD-1 limits the natural antitumor immunity. (A) PD-1 expression by CD11a$^{high}$ CD8 T cells isolated from subcutaneously implanted B16-OVA tumors. (B) Kinetics and distribution of PD-1$^+$ CD11a$^{high}$ CD8 T cells in tumor tissues, draining lymph nodes (DLN) and non-draining lymph nodes (NDLN) and spleen. (C) Subcutaneous implanted B16-OVA tumor growth in wild type (WT) and PD-1 knockout (KO) mice. Data show the mean size of tumors plus SD (n=4). (D) Percentages of CD11a$^{high}$ CD8 T cells in tumor tissues on day 12 after tumor injection in WT and PD-1 KO mice.

High Expression of PD-1 by CD11a$^{high}$ CD8 T Cells Compromises the Ability to Control Tumor Growth Although functional tumor-reactive CD11a$^{high}$ CD8 T cells were identified within tumors, they were unable to control tumor growth. Several factors could contribute to compromised anti-tumoral activity including the possibility that T cells might become exhausted following chronic antigen exposure within the tumor bed. To examine this scenario, the expression of PD-1, an immunoregulatory receptor expressed by exhausted T cells (Barber et al., *Nature*, 439:682-687 (2006)) and tumor-associated T cells (Thompson et al., *Clinical Cancer Research*, 13:1757-1761 (2007); Zhang et al., *Blood*, 114:1545-1552 (2009); Mumprecht et al., *Blood*, 114:1528-1536 (2009); and Ahmadzadeh et al., *Blood*, 114:1537-1544 (2009)), on CD11a$^{high}$ CD8 T cells isolated from tumors was determined. CD11a$^{high}$ CD8 T cells isolated from established tumors expressed elevated levels of PD-1 compared to naïve CD8 T cells (FIG. 2A). In contrast, CD11a$^{low}$ CD8 T cells did not express PD-1. The expression of PD-1 was first detected on CD11a$^{high}$ CD8 T cells isolated from day 7 tumors and maintained within tumors until day 28 (FIG. 2B). To test whether the quick and persistent expression of PD-1 by CD11a$^{high}$ CD8 T cells impairs the antitumor activity of tumor-reactive CD11a$^{high}$ CD8 T cells, B16-OVA tumor cells were injected into naïve PD-1 KO mice, and tumor growth was measured. B16-OVA growth was significantly delayed in PD-1 KO mice compared to WT mice (FIG. 2C). These results indicated that PD-1 negatively regulates natural antitumor immunity. To ascertain whether increased natural antitumor immunity is related to the presence of CD11a$^{high}$ CD8 T cells, the frequencies of CD11a$^{high}$ CD8 T cells within tumors established in PD-1 KO mice and wild-type mice on day 12, when their tumors grew to the same size, were measured. Interestingly, CD11a$^{high}$ CD8 T cells increased 2-3 fold within tumors in PD-1 KO mice compared with wild type mice (FIG. 2D). These results suggested that tumor-reactive CD11a$^{high}$ CD8 T cells are functional but are compromised in their capacity to control tumor growth due to high and persistent expression of PD-1.

Figure 3:
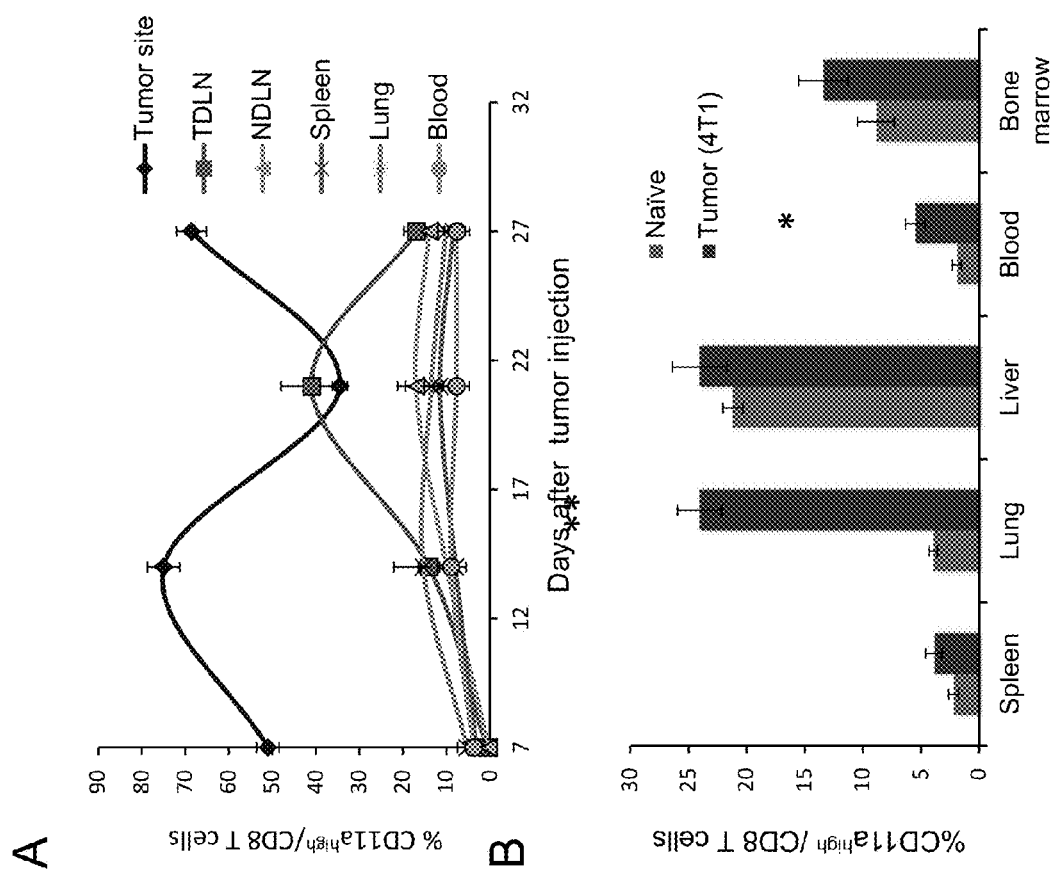
FIG. 3. CD11a$^{high}$ CD8 T cells identified at primary and metastatic tumor sites. 4T1 mouse breast tumor cells (1×10$^5$) were injected subcutaneously (A) or intravenously (B). (A) The kinetics and distribution of CD11a$^{high}$ CD8 T cells in multiple tissues of mice with primary subcutaneously implanted 4T1 tumors. TDLN, tumor draining lymph nodes, NDLN, non-draining lymph nodes. (B) The distribution of CD11a$^{high}$ CD8 T cells in multiple tissues of naive mice and mice with 4T1 tumors on day 7 after intravenously tumor injection. *p<0.05, **p<0.01 compared with naïve mice. Three mice per group, one of three experiments is shown.

Tumor-Induced CD11a$^{high}$ CD8 T Cells are Present at Primary and Metastatic Tumor Sites Tumor-specific, functional CD11a$^{high}$ CD8 T cells were identified using a tumor model with a surrogate tumor antigen. To extend this observation to a tumor antigen undefined system and to detect tumor-reactive CD8 T cells at primary and secondary (metastatic) tumor sites, an antigen undefined mouse breast tumor (4T1) was used, which develops a tumor after subcutaneously injection and forms metastasis (preferentially in the lung) after intravenous infusion. The frequency of CD11a$^{high}$ CD8 T cells within subcutaneously inoculated 4T1 tumors was examined first. The frequency of CD11a$^{high}$ CD8 T cells within 4T1 tumors exhibited similar kinetics as was observed for B16-OVA tumors. CD11a$^{high}$ CD8 T cells were first detectable on day 7 after tumor injection, increasing within 4T1 tumors towards day 14, and declining thereafter. As with the B16-OVA system, CD11a$^{high}$ CD8 T cells increased in frequency from days 21-27 (FIG. 3A). CD11a$^{high}$ CD8 T cells only transiently appeared in draining lymph nodes on day 21 following tumor injection and did not appreciably populate in spleen, lung, or peripheral blood (FIG. 3A).

To detect whether $CD11a^{high}$ CD8 T cells were induced at the metastatic sites of 4T1 tumors, lymphocytes were isolated and analyzed from multiple organs after intravenously infusion of 4T1 tumor cells, a model of systemic tumor metastasis. On day 7 after tumor infusion, the number of $CD11a^{high}$ CD8 T cells significantly increased in the lung (22.7% of CD8 T cells, p<0.01) and in blood (3.9% of CD8 T cells, p<0.05), but the numbers were unchanged in the spleen, liver, and bone marrow compared with naïve mice (FIG. 3B). Unexpectedly, the largest percentages of $CD11a^{high}$ CD8 T cells were observed in livers from tumor bearing or naïve mice. As the liver is a main location for deposition and depletion of naturally or endogenously activated CD8 T cells (Crispe, Immunology, 3:51-62 (2003); and Dong et al., Immunity, 20:327-336 (2004)), the accumulation of $CD11a^{high}$ CD8 T cells in the liver suggested that $CD11a^{high}$ CD8 T cells are representative of antigen-primed T cell population.

Figure 4:
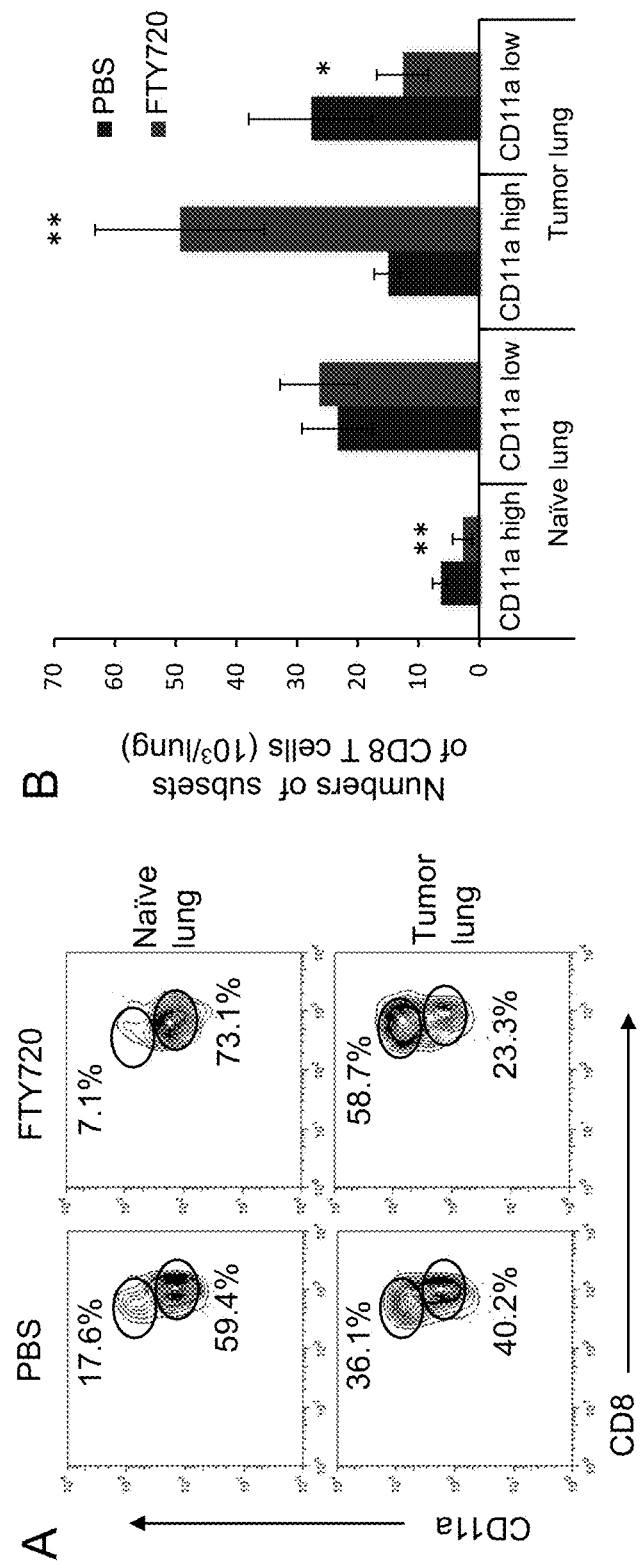
FIG. 4. In situ expansion of CD11a$^{high}$ CD8 T cells within tumor site. 4T1 tumor cells were intravenously injected into Balb/c mice with or without intraperitoneal injection of 1 mg/kg of FTY720. On day 7 after tumor injection, lymphocytes were isolated from the lung of tumor mice and naïve mice that also received FTY720. (A) Percentages of CD 11a$^{high}$ and CD11a$^{low}$ CD8 T cells in the lungs. (B) Absolute numbers (mean±SD) of CD11a$^{high}$ and CD11a$^{low}$ CD8 T cells in the lung (n=3). *p=0.022, **p=0.013 compared with control PBS groups. One of two independent experiments is shown.

To ascertain whether $CD11a^{high}$ CD8 T cells represent in situ tumor induction or reflect a migratory influx following activation from other tumor bearing sites, FTY720, a molecule known to inhibit lymphocyte emigration from lymphoid organs (Brinkmann et al., Transplantation, 72:764-769 (2001)), was injected following infusion of tumor cells. After injection of FTY720 with or without tumor cells, the frequencies of $CD11a^{high}$ CD8 T cells in the lung of naïve mice and tumor-bearing mice were measured and compared. In naïve mice, FTY720 blocked the accumulation of $CD11a^{high}$ CD8 T cells in both frequency and numbers, but not $CD11a^{low}$ CD8 T cells, in the lung (FIG. 4), suggesting that $CD11a^{high}$ CD8 T cells may have an origin in lymphoid organs. However, in tumor-bearing mice, FTY720 did not block the accumulation of $CD11a^{high}$ CD8 T cells in the lung (FIG. 4). Unexpectedly, both the frequency and numbers of $CD11a^{high}$ CD8 T cells increased in the lung after FTY720 injection. According to the decrease of $CD11a^{low}$ CD8 T cells in the lung of tumor mice after FTY720 injection, the increase of $CD11a^{high}$ CD8 T cells suggested that the majority of resident rather than migrated naïve $CD11a^{low}$ CD8 T cells are induced by tumor cells to become $CD11a^{high}$ CD8 T cells that are undergoing expansion in the lung.

Figure 5:
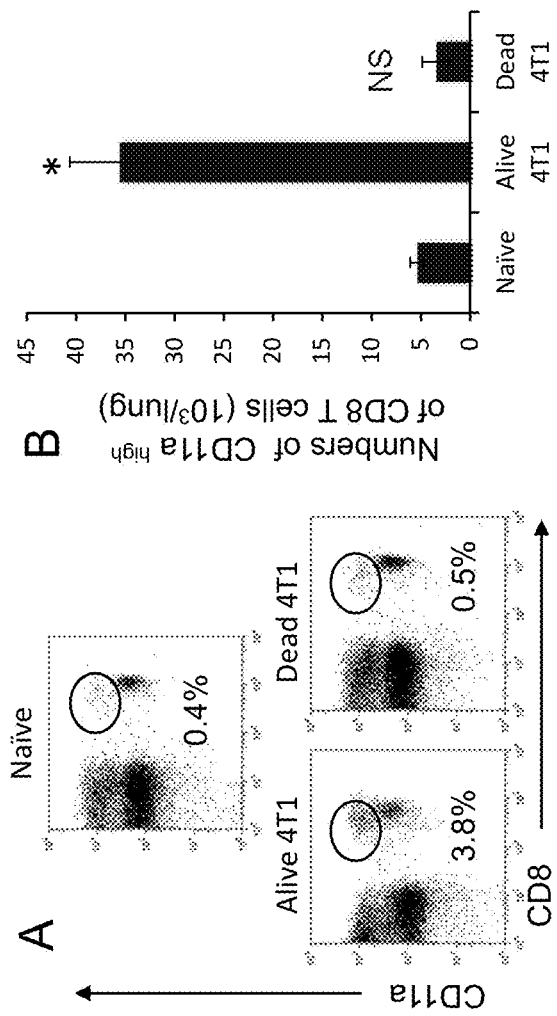
FIG. 5. Live tumor cells induce CD11a$^{high}$ CD8 T cell responses. Alive or lethally irradiated 4T1 tumor cells (loss of ability to infiltrate target tissues) were intravenously injected into naïve Balb/c mice. On day 7 after tumor injection, lymphocytes were isolated from the lungs of tumor mice or naïve control mice. (A) The percentages of CD11a$^{high}$ CD8 T cells in the lung (target tissues). (B) Absolute numbers (mean±SD) of CD 11a$^{high}$ CD8 T cells in the lung (n=3). *p=0.0004, NS (non-significant) compared with naive groups. One of two independent experiments is shown.

To further confirm that the active infiltration of 4T1 tumor cells is driving CD8 T cell activation, either lethally irradiated 4T1 tumor cells, which have lost the ability to infiltrate tissues, or viable 4T1 tumor cells were intravenously injected into naïve mice. On day 7 after tumor injection, $CD11a^{high}$ CD8 T cells increased in the lungs of mice injected with live 4T1 tumor cells, but not in the lungs of mice infused with dead 4T1 tumor cells (FIG. 5). Thus, it was concluded that $CD11a^{high}$ CD8 T cells are local T cells responding to active infiltration of tumor cells at both primary and metastatic tumor sites.

Figure 6:
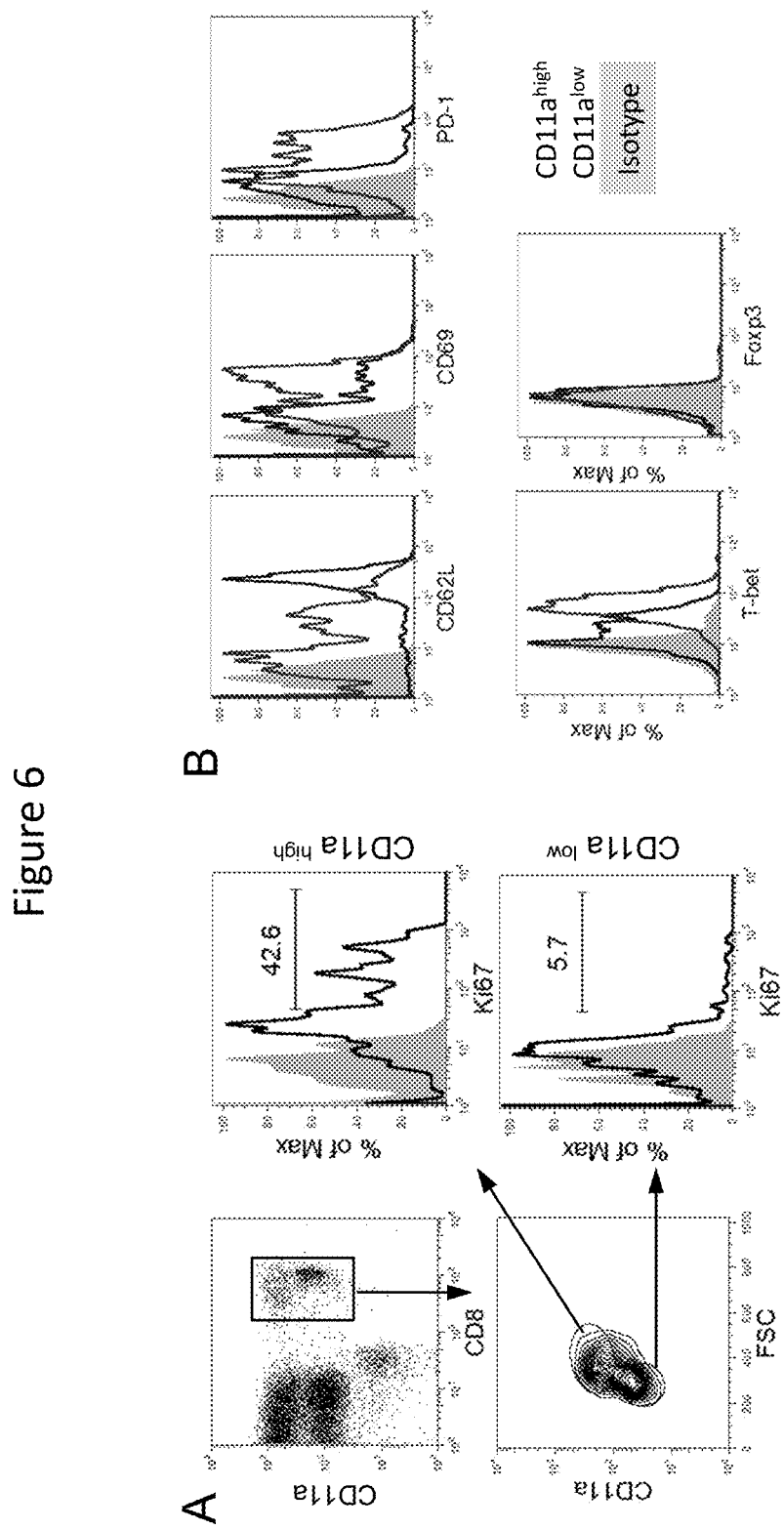
FIG. 6. Phenotype of tumor-induced CD11a$^{high}$ CD8 T cells. Lymphocytes were isolated from the lung of mice on day 7 after intravenously injection of 4T1 tumor cells. (A) Proliferation of CD11a$^{high}$ CD8 T cells measured by their larger forward light scatter (FSC) and intranuclear expression of Ki67. (B) Surface expression of CD62L, CD69 and PD-1 and intracellular expression of T-bet and Foxp3 by CD11a$^{high}$ and CD11a$^{low}$ CD8 T cells. One of three independent experiments is shown.
Figure 7:
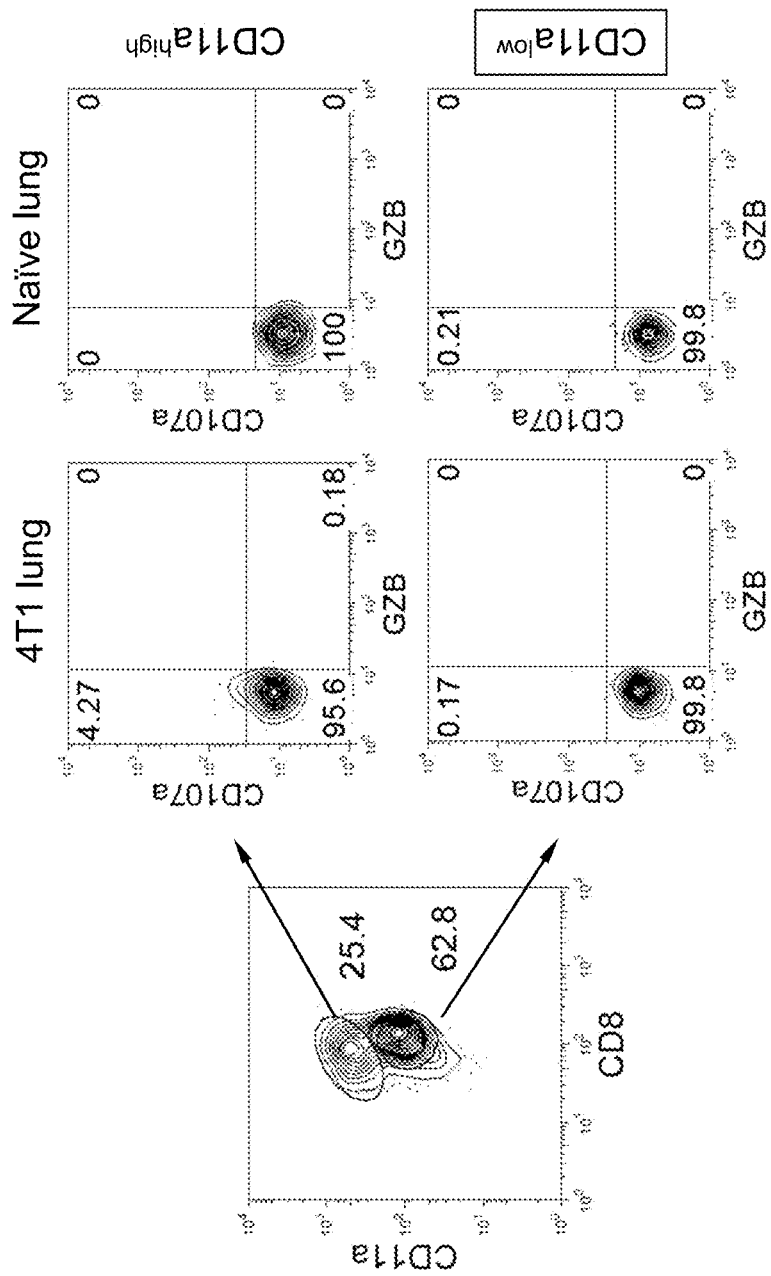
FIG. 7. Function of CD11a$^{high}$ CD8 T cells within 4T1 tumor tissues. Lymphocytes were isolated from the lung of naïve mice or mice on day 7 after intravenous injection of 4T1 tumor cells. CTL function of CD 11a$^{high}$ or CD 11a$^{high}$ CD8 T cells was assessed by measuring degranulation (CD107a expression) and intracellular production of IFN-gamma following a 4-hour ex vivo stimulation with PMA/ionomycin. One of three independent experiments is shown.

Poor Immunogenic Tumor-induced $CD11a^{high}$ CD8 T Cells are Proliferative Effector Cells but Lack of Robust CTL Function The accumulation of $CD11a^{high}$ CD8 T cells at both primary and metastatic sites of 4T1 tumor was striking because the 4T1 tumor is postulated to be a poorly immunogenic tumor (Lewis et al., Cancer Research, 65:2938-2946 (2005)). The following was performed to analyze the phenotype and function of $CD11a^{high}$ CD8 T cells isolated from 4T1 tumor tissues. $CD11a^{high}$ CD8 T cells were proliferative cells in that the cells were large blasts (larger forward light scatter in flow cytometry) and expressed Ki67, a nuclear protein linked to cell proliferation (FIG. 6A). Phenotype analysis (FIG. 6B) revealed that $CD11a^{high}$ CD8 T cells were activated T cells ($CD62L^{low}$, $CD69^{high}$, $PD-1^{high}$). $CD11a^{high}$ CD8 T cells expressed higher levels of transcriptional factor T-bet that determines the differentiation of Th1 or CTLs (Harrington et al., J. Exp. Med., 191:1241-1246 (2000)), but did not express Foxp3, a master factor for T regulatory cells (FIG. 6B), suggesting that $CD11a^{high}$ CD8 T cells underwent effector differentiation. To examine whether the cells acquired effector function, degranulation (CD107a expression) and granzyme B (an executive molecule of CTL) expression by $CD11a^{high}$ CD8 T cells induced by 4T1 tumors in the lung were measured. Because the tumor antigens are not defined in 4T1 tumor cells, phorbol myristate acetate (PMA)/ionomycin, which bypasses TCR signaling, were used to activate T cell by activating DAG and calcium release (Truneh et al., Nature, 313:318-320 (1985)). Compared with CD8 T cells from naïve mice, tumor-induced $CD11a^{high}$ CD8 T cells slightly increased CD107a expression, but did not produce granzyme B (FIG. 7). These results suggested that $CD11a^{high}$ CD8 T cells induced by poorly immunogenic tumors are proliferative differentiated effector cells that lack robust CTL function.

$CD11a^{high}$ CD8 T Cells are Induced by Spontaneous Tumors

Figure 8:
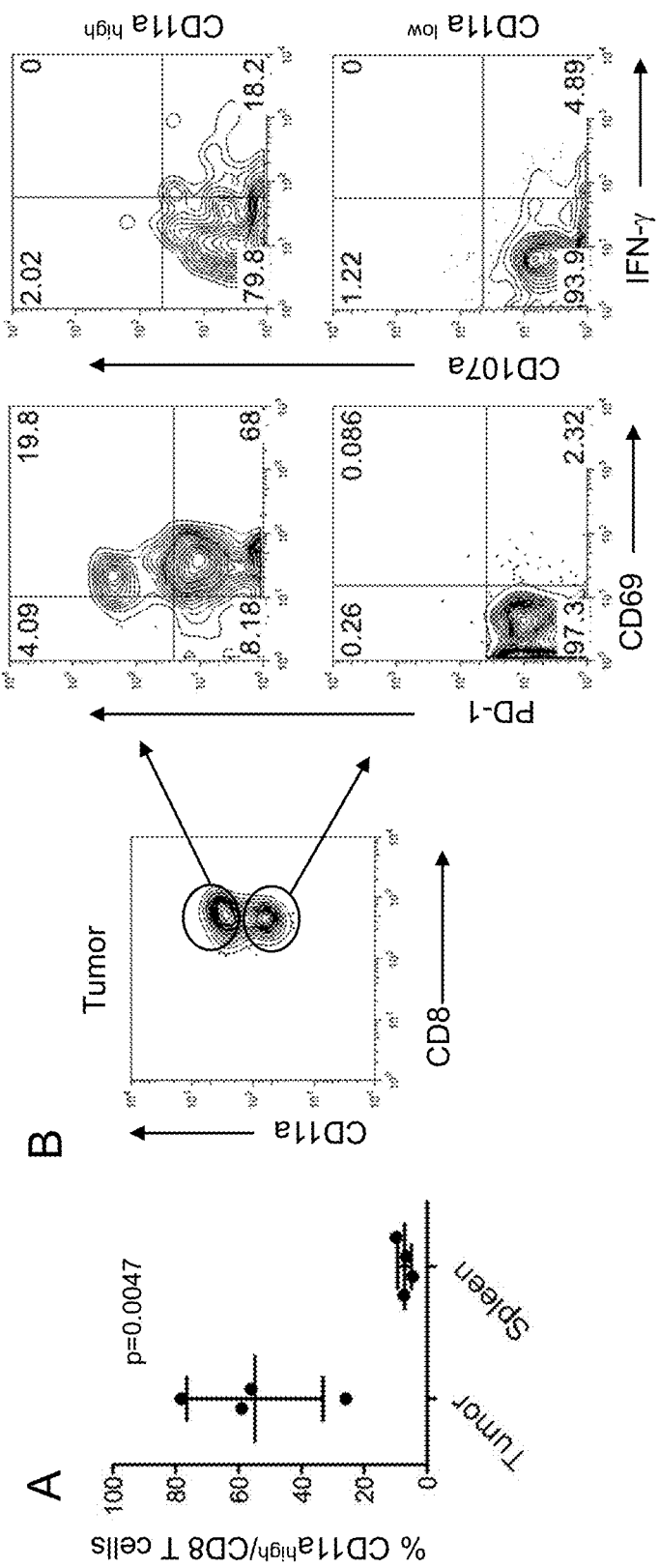
FIG. 8. CD11a$^{high}$ CD8 T cells identified within spontaneous tumors. Lymphocytes were isolated from the breast tissues with tumors or spleen of Blab-neuT mice at 15-18 weeks of age. (A) Percentage of CD11a$^{high}$ CD8 T cells within tumors and spleen. (B) Phenotype and function of CD11a$^{high}$ and CD11a$^{low}$ CD8 T cells isolated from tumor tissues. Degranulation (CD107a expression) and IFN-γ production were measured following a 4-hour ex vivo stimulation with PMA/ionomycin. One of three independent experiments is shown.

Although up-regulation of CD11a on CD8 T cells is not affected by inflammation (Rai et al., J. Immunol., 183:7672-7681 (2009)), the injected tumor cells may cause acute CD8 T cell responses to large tumor antigen exposure leading to accumulation of $CD11a^{high}$ CD8 T cells at the tumor site. As spontaneous tumors provide chronic and persistence antigen exposure for CD8 T cells, it was important to determine if it would be possible to detect accumulation of $CD11a^{high}$ CD8 T cells within spontaneous tumors. Lymphocytes were isolated from spontaneous breast tumors generated in female Balb-neuT mice carrying the activated HER-2/neu oncogene (Boggio et al., J. Exp. Med., 188: 589-596 (1998)). At 17-20 weeks of age when the mammary glands display visible invasive carcinoma (Nava-Parada et al., Cancer Research, 67:1326-1334 (2007)), a significant increase of $CD11a^{high}$ CD8 cells within tumor tissues, but not in spleen, of the same host was measured (FIG. 8A). In addition, $CD11a^{high}$ CD8 T cells expressed high levels of CD69 and PD-1 (FIG. 8B). Functionally, spontaneous tumor-induced $CD11a^{high}$ CD8 T cells slightly increased IFN-γ production, but did not express CD107a after ex vivo stimulation with PMA/ionomycin (FIG. 8C). But, their CTL function could not be induced by a high affinity Neu antigen peptide (p66) (Nava-Parada et al., Cancer Research, 67:1326-1334 (2007)). As CD69 is a recent T cell activation maker and PD-1 is a marker of T cell exhaustion, these results suggested diversity among $CD11a^{high}$ CD8 T cells, reflecting the presence of both recently activated and exhausted T subpopulations. The dysfunction of these two populations was consistent with their failure in control the growth of spontaneous tumors.

Tumor-Reactive $PD-1^+$ $CD11a^{high}$ CD8 T Cells Increased in the Blood of Melanoma Patients To test whether $CD11a^{high}$ CD8 T cells consist of tumor specific CD8 T cells in cancer patients, CD8 T cells were analyzed from ten patients with stage IV melanoma. To define tumor-specific CD8 T cells, human CD8 T cells from melanoma patients were co-stained with HLA-A2/MART-1 tetramer detecting MART-1 (a melanoma differentiation antigen)-specific CD8 T cells. More Mart-1-specific T cells were identified in $CD11a^{high}$ subset of CD8 T cells than in $CD11a^{low}$ subsets (FIGS. 9A and 9B), suggesting that $CD11a^{high}$ CD8 T cells consist of tumor-specific CD8 T cells. Analyzing the expression of immunoregulatory receptors (PD-1 and CTLA-4), it was determined that $CD11a^{high}$ CD8

Figure 9:
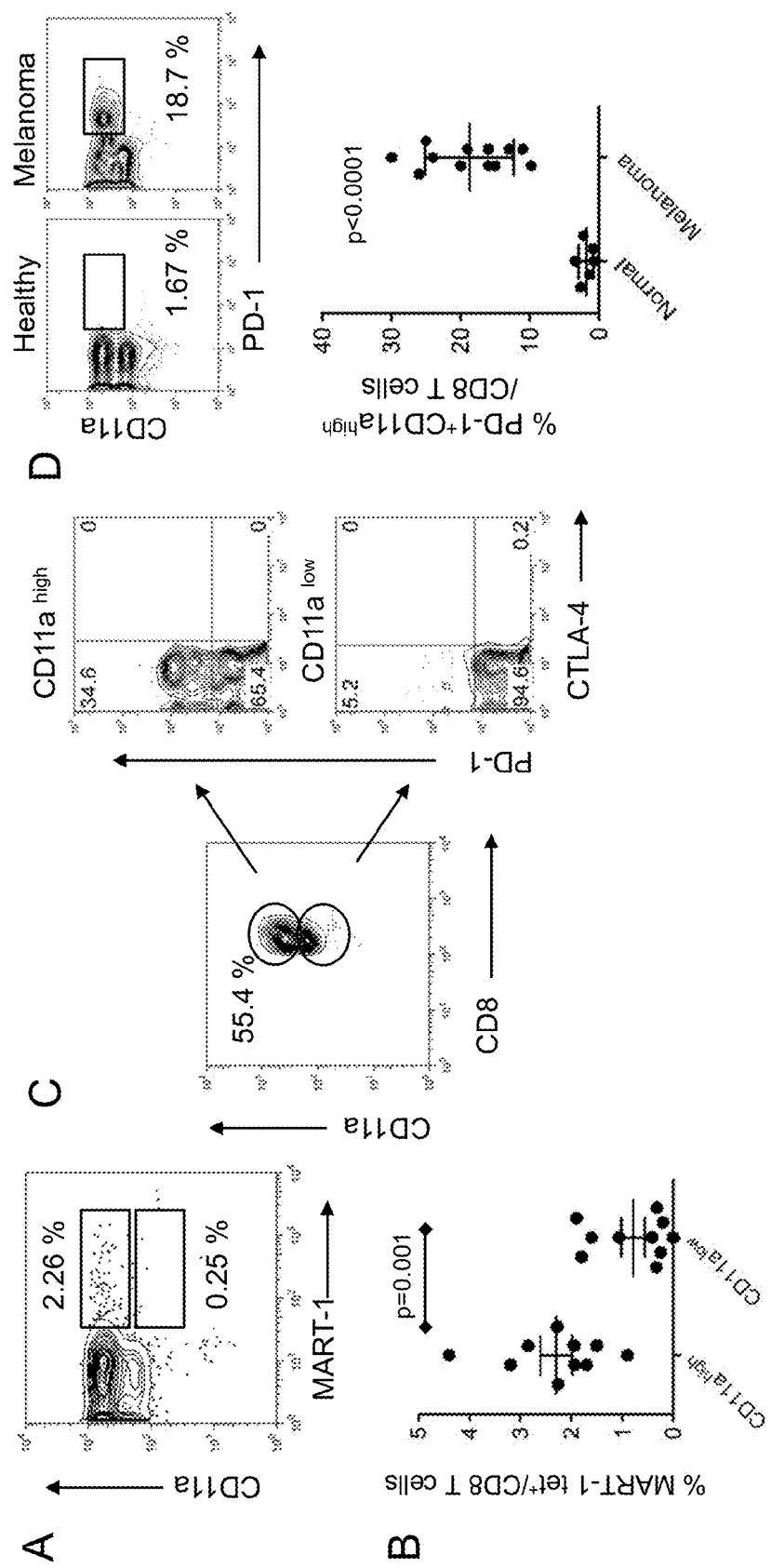
FIG. 9. PD-1$^+$ CD11a$^{high}$ CD8 T cells increased in the peripheral blood of melanoma patients. Peripheral blood mononuclear cells (PBMCs) were isolated from healthy donors or patients with stage IV melanoma. (A) Tumor antigen specificity of CD11a$^{high}$ CD8 T cells in PBMCs of melanoma patients. Numbers are the percent of MART-1 tet$^+$ in CD11a$^{high}$ and CD11a$^{low}$ CD8 T cells. (B) Percentages of MART-1-tet$^+$CD 11a$^{high}$ and MART-1-tet$^+$ CD11a$^{low}$ cells in total CD8 T cells. Data show mean±SEM, n=10. (C) Expression of PD-1 and CTLA-4 by CD11a$^{high}$ and CD11a$^{low}$ CD8 T cells of PBMCs from melanoma patients. (D) Frequency of PD-1$^+$CD11a$^{high}$ per total CD8 T cells in PBMCs of healthy donors (n=6) and melanoma patients (n=12).

T cells expressed elevated levels of PD-1, but not CTLA-4, compared with CD11a$^{low}$ CD8 T cells (FIG. 9C). In comparison with healthy donors, the frequency of PD-1$^+$ CD11a$^{high}$ CD8 T cells significantly increased in the peripheral blood of patients with stage IV melanoma (18.7±1.8% vs. 1.7±0.4% of healthy donor, p<0.0001, FIG. 9D). At this advanced stage of melanoma, accumulation of PD-1$^+$ CD8 T cells may reflect the dysfunctional state of tumor-reactive CD8 T cells in these patients. These results suggested that in melanoma patients, most of the tumor specific CD8 T cells are CD11a$^{high}$ CD8 T cells that co-express elevated levels of PD-1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cancer, wherein said method comprises:
   (a) identifying said mammal as having an elevated level of PD-1$^+$/CD11a$^{high}$ CD8 T cells within a blood, body fluid, or tumor samplerelative to a reference level of PD-1$^{30}$ /CD11a$^{high}$ CD8 T cells in mammals without cancer, and
   (b) administering a PD-1 inhibitor to said mammal, wherein naturally-occurring tumor-reactive CD8 CTLs within a PD-1$^+$/CD11a$^{high}$ CD8 T cell population of said mammal exert an anti-cancer effect against said cancer.

2. The method of claim 1, wherein said mammal is a human.

3. The method of claim 1, wherein said elevated level is determined using flow cytometry.

4. The method of claim 1, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

5. A method for treating cancer, wherein said method comprises administering a PD-1 inhibitor to a mammal identified as having an elevated level of PD-1$^+$/CD11a$^{high}$ CD8 T cells within a blood, body fluid, or tumor sample relative to a reference level of PD-1$^{30}$ /CD11a$^{high}$ CD8 T cells in mammals without cancer, wherein naturally-occurring tumor-reactive CD8 CTLs within a PD-1$^+$/CD11a$^{high}$ CD8 T cell population of said mammal exert an anti-cancer effect against said cancer.

6. The method of claim 5, wherein said mammal is a human.

7. The method of claim 5, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

* * * * *

UNITED STATES PATENT AND TRADEMARK OFFICE
CERTIFICATE OF CORRECTION

PATENT NO. : 9,302,005 B2  
APPLICATION NO. : 14/192376  
DATED : April 5, 2016  
INVENTOR(S) : Haidong Dong et al.

It is certified that error appears in the above-identified patent and that said Letters Patent is hereby corrected as shown below:

In the Claims

Column 11, line 26 (Claim 1), please delete "samplerelative" and insert -- sample relative --, therefor;

Column 11, line 27 (Claim 1), please delete "PD-1$^{30}$" and insert -- PD-1$^{+}$ --, therefor;

Column 12, line 17 (Claim 5), please delete "PD-1$^{30}$" and insert -- PD-1$^{+}$ --, therefor.

Signed and Sealed this  
Thirty-first Day of May, 2016

Michelle K. Lee  
*Director of the United States Patent and Trademark Office*